(12) United States Patent
Li

(10) Patent No.: US 12,361,756 B2
(45) Date of Patent: Jul. 15, 2025

(54) ARTIFICIAL INTELLIGENCE-ASSISTED EVALUATION METHOD FOR AESTHETIC MEDICINE AND EVALUATION SYSTEM USING SAME

(71) Applicant: Chih-Wei Li, New Taipei (TW)

(72) Inventor: Chih-Wei Li, New Taipei (TW)

(\*) Notice: Subject to any disclaimer, the term of this patent is extended or adjusted under 35 U.S.C. 154(b) by 504 days.

(21) Appl. No.: 17/577,146

(22) Filed: Jan. 17, 2022

(65) Prior Publication Data

US 2022/0230471 A1 Jul. 21, 2022

Related U.S. Application Data

(60) Provisional application No. 63/137,767, filed on Jan. 15, 2021.

(51) Int. Cl.
*G06T 7/00* (2017.01)
*G06N 3/08* (2023.01)
*G06V 10/44* (2022.01)
*G06V 10/77* (2022.01)
*G06V 40/16* (2022.01)
(Continued)

(52) U.S. Cl.
CPC ............. *G06V 40/176* (2022.01); *G06N 3/08* (2013.01); *G06T 7/0012* (2013.01); *G06V 10/44* (2022.01); *G06V 10/7715* (2022.01); *G06V 40/168* (2022.01); *G06V 40/175* (2022.01); *G16H 20/17* (2018.01); *G16H 70/40* (2018.01); *G06T 2207/30088* (2013.01)

(58) Field of Classification Search
CPC ..................................................... G16H 20/40
See application file for complete search history.

(56) References Cited

U.S. PATENT DOCUMENTS

| 9,336,268 B1* | 5/2016 | Moudy | .................. G06F 40/30 |
| 2010/0189357 A1* | 7/2010 | Robin | .................. G06T 11/001 |
| | | | 382/195 |

(Continued)

FOREIGN PATENT DOCUMENTS

| CN | 107007257 | 8/2017 |
| TW | 202044279 | 12/2020 |

*Primary Examiner* — Di Xiao
(74) *Attorney, Agent, or Firm* — WPAT, PC

(57) ABSTRACT

An artificial intelligence (AI)-assisted evaluation method for aesthetic medicine and an evaluation system are provided. An AI aesthetic medicine identification and analysis module is used. An AI facial expression evaluation module provides a real-time facial expression evaluation result of a subject. The real-time facial expression evaluation result is inputted into the AI aesthetic medicine identification and analysis module. The AI aesthetic medicine identification and analysis module optionally cooperates with at least one of a medical knowledge rule module and an aesthetic medicine auxiliary evaluation result historical database to perform an AI aesthetic medicine identification and analysis process. Then, the AI aesthetic medicine identification and analysis module generates and outputs a real-time aesthetic medicine auxiliary evaluation result. According to the real-time aesthetic medicine auxiliary evaluation result, an aesthetic medicine behavior is carried out. Consequently, the personalized aesthetic therapeutic effect can be achieved.

16 Claims, 13 Drawing Sheets

(51) Int. Cl.
*G16H 20/17* (2018.01)
*G16H 70/40* (2018.01)

(56) References Cited

U.S. PATENT DOCUMENTS

| | | | |
|---|---|---|---|
| 2015/0157259 A1* | 6/2015 | Bradu | A61B 5/743 |
| | | | 600/476 |
| 2018/0211102 A1* | 7/2018 | Alsmadi | G06V 40/171 |
| 2021/0282747 A1* | 9/2021 | Poland | A61B 8/42 |
| 2022/0019775 A1* | 1/2022 | Chen | G06N 5/01 |
| 2023/0036903 A1* | 2/2023 | Ma | G06V 40/162 |

\* cited by examiner

| Subject name | Basic data B | | Historical face image emotion evaluation result A' | | | | | Personal facial feature P | | | Functional medical anatomy rule R1 | Dynamic medical anatomy rule R2 | ... | Evaluated treatment site result combination and priority order | | Type and dose of injected filler | |
|---|---|---|---|---|---|---|---|---|---|---|---|---|---|---|---|---|---|
| | Gender B1 | Age B2 | Static facial action coding information A1 | Dynamic facial action coding information A2 | Emotional indicator A31 | Emotional indicator A32 | Emotional indicator A33 | Feature P1 | Feature P2 | Feature P3 | | | | Priory C1 | Priory C2 | Type D | Dose U |
| Subject 1 | F | 28 | AU1 ... AUn | AU1' ... AUn' | 35.2% | 14.1% | 17.7% | P11 | P22 | P33 | R11 | R22 | ... | AU1 | AU1 + AU4 | X11 | 8 |
| Subject 2 | F | 33 | AU1 ... AUn | AU1' ... AUn' | 13.9% | 9.5% | 7.2% | P13 | P24 | P32 | R11 | R21 | ... | AU1 + AU15 + AU17 | AU15 + AU17 | X21 + Y21 | 8(X11) + 4(Y21) + 4(X11)+1(Y21) |
| Subject 3 | F | 45 | AU1 ... AUn | AU1' ... AUn' | 6.8% | 14.0% | 5.0% | P12 | P21 | P31 | R13 | R24 | ... | AU15 + AU17 | AU1 + AU15 | X31 | 4(X31) + 4(X31) |
| Subject 4 | M | 56 | AU1 ... AUn | AU1' ... AUn' | 26.8% | 9.8% | 12.3% | P14 | P23 | P33 | R14 | R23 | ... | AU1 + AU2 + AU15 | AU2 + AU15 | X42 + Y43 + Z41 | 8(X42) + 4(Y43) + 2(Z41) |

FIG. 3

| AU | Trace | Little | Obvious | Severe | Maximum |
|---|---|---|---|---|---|
| 01 | | | C | | |
| 02 | | | | | |
| 04 | | | | D | |
| 05 | | | | | |
| 06 | | | | | |
| 07 | | | | | |
| 09 | | | | | |
| 10 | | | | | |
| 12 | | | | | |
| 14 | | | | | |
| 15 | | | C | | |
| 17 | | | | D | |
| 18 | | | | | |
| 20 | | | | | |
| 22 | | | | | |
| 24 | | | | | |
| 25 | | | | | |
| 26 | | | | | |
| 27 | | | | | |
| 43 | | | | | |

ARTIFICIAL INTELLIGENCE-ASSISTED EVALUATION METHOD FOR AESTHETIC MEDICINE AND EVALUATION SYSTEM USING SAME

FIELD OF THE INVENTION

The present invention relates to an artificial intelligence (AI)-assisted evaluation method for aesthetic medicine and an evaluation system, and more particularly to an AI-assisted evaluation method based on a real-time facial expression evaluation result and applied to aesthetic medicine and an AI-assisted evaluation system using the method.

BACKGROUND OF THE INVENTION

Nowadays, aesthetic medicine becomes very popular. Especially, the facial micro-surgery aesthetic medicine has been widely favored and accepted by people of all ages.

The treatment method of the facial micro-surgery aesthetic medicine mainly relies on the doctor's own medical expertise and knowledge. The treatment method is performed according to the general or normalized standard procedures, or some individual judgments of the doctor's own practice experience are added.

However, the conventional treatment method still has some drawbacks. For example, due to the lack of the deep customization considerations, there is often a gap between the actual aesthetic treatment result and the expected treatment result. Especially, since the facial micro-expressions are contributed to the muscle micro-movements accumulated by long-term expression habits, these potential facial muscle changes are not easy to be observed by the naked eye in a short time. Consequently, there is often a big difference between the actual aesthetic treatment result and the expected treatment result.

Moreover, due to the doctor's wrong judgments, some actual aesthetic medical treatment results lead to inferior therapeutic effects after surgery. Consequently, more medical treatment disputes and medical treatment deficiencies occur.

Therefore, it is an important issue for the aesthetic medical industry to provide more and better methods and tools to assist in the personalized aesthetic medical needs. For solving the problems of the conventional technologies, the applicant has proposed a technical solution about an artificial intelligence-assisted evaluation method and an evaluation system in Taiwan Patent Application No. TW109115444.

In order to further optimize the relevant technical contents, the applicant further improves the method of acquiring the real-time facial expression evaluation result and provides an optimization solution as described later in the descriptions of the present invention.

SUMMARY OF THE INVENTION

An object of the present invention provides an AI-assisted evaluation method based on a real-time facial expression evaluation result and applied to aesthetic medicine according to personalized aesthetic medical needs and an AI-assisted evaluation system using the method. Consequently, the drawbacks of the conventional technologies can be overcome.

In accordance with the implementation concepts of the present invention, an AI facial expression evaluation module is used to acquire a personalized real-time facial expression evaluation result. Then, an AI aesthetic medicine identification and analysis process is performed according to the personalized real-time facial expression evaluation result. After the AI aesthetic medicine identification and analysis module cooperates with a medical knowledge rule module and an aesthetic medicine auxiliary evaluation result historical database, a real-time aesthetic medicine auxiliary evaluation result is provided. Consequently, the customized and real-time personalized aesthetic medicine recommendation can be given.

In accordance with a first embodiment of the present invention, an AI-assisted evaluation method for aesthetic medicine is provided. The AI-assisted evaluation method at least includes the following steps. In a step (a), a real-time facial expression evaluation result of a subject is provided. In a step (b), an AI aesthetic medicine identification and analysis process is performed on the real-time facial expression evaluation result according to at least one of a medical knowledge rule module and an aesthetic medicine auxiliary evaluation result historical database. Consequently, a real-time aesthetic medicine auxiliary evaluation result is generated. The step (a) at least includes the following steps. In a step (a1), an AI image detection process is performed to acquire a real-time face image of the subject. In a step (a2), an AI image calibration and feature extraction process is performed according to the real-time face image, so that a facial surface and geometric feature information is acquired. In a step (a3), an AI facial action coding process is performed according to the facial surface and geometric feature information, so that plural pieces of facial action coding information are acquired. In a step (a4), an AI facial emotion recognition process is performed according to the plural pieces of facial action coding information. Consequently, a proportional distribution and combination information of plural emotional indicators corresponding to the real-time face image is acquired and the real-time face image emotion evaluation result is generated.

Preferably, after the step (b), the AI-assisted evaluation method further includes a step (c) of feeding back and storing the real-time aesthetic medicine auxiliary evaluation result into the at least one of the medical knowledge rule module and the aesthetic medicine auxiliary evaluation result historical database.

Preferably, the real-time aesthetic medicine auxiliary evaluation result at least contains an evaluated treatment site result combination and priority order for the subject, or the real-time aesthetic medicine auxiliary evaluation result at least contains the evaluated treatment site result combination and priority order and a type and a dose of an injected filler.

Preferably, the medical knowledge rule module further includes a functional medical anatomy rule and a dynamic medical anatomy rule.

Preferably, the AI image detection process is performed according to an AI machine learning method. The AI machine learning method includes a boundary detection algorithm corresponding to Haar-Like features in combination with an adaptive boosting machine learning method, or the AI machine learning method includes a histogram of oriented gradients (HOG) method in cooperation with a support vector machine (SVM) machine learning method.

Preferably, in the step (a2), the AI image calibration and feature extraction process at least includes following steps. In a step (a21), an AI facial key point labelling process is performed according to the real-time face image, so that a facial key point labelling information is acquired. In a step (a22), a facial image calibration process is performed according to the facial key point labelling information, so that a normalized facial image information is acquired. In a step (a23), a facial image feature extraction process is performed according to the facial key point labelling information and the normalized facial image information, so that the facial surface and geometric feature information is acquired.

Preferably, before the AI facial key point labelling process is performed, a machine learning method is performed to train a facial key point model of the AI facial key point labelling process according to a specified number of training data sets.

Preferably, in the facial image calibration process, at least an affine transformation technology is used to eliminate errors caused by different postures in the facial key point labelling information and unify size and presentation of the face image, so that the normalized facial image information is acquired.

Preferably, the facial image feature extraction process at least includes a facial image surface feature extraction process and a facial image geometric feature extraction process. The facial image surface feature extraction process is performed through a histogram of oriented gradients (HOG) method to obtain multi-dimensional vector data, and a principal component analysis (PCA) technology is used to reduce a vector data amount and retain an important facial image surface feature information. The facial image feature geometric extraction process is performed to acquire a facial image geometric feature information according to the facial key point labelling information.

Preferably, before the AI facial action coding process is performed, a machine learning method is performed to train a facial action coding model of the AI facial action coding process according to a specified number of training data sets and a facial action coding system (FACS).

Preferably, the facial action coding model is trained in different scenarios including a static expression scenario and/or a dynamic expression scenario, so that a static facial action coding information and a dynamic facial action coding information are respectively acquired.

Preferably, before the AI facial emotion recognition process is performed, another machine learning method is employed to train a facial emotion recognition model of the AI facial emotion recognition process according to at least one of an emotional valance, an emotional arousal and the plural emotional indicators in combination with the above facial action coding system.

Preferably, the aesthetic medicine auxiliary evaluation result historical database contains plural aesthetic medical auxiliary evaluation results. Each of the plural aesthetic medical auxiliary evaluation results at least contains a subject name, a basic data, a historical face image emotion evaluation result, a personal facial feature, a functional medical anatomy rule and a dynamic medical anatomy rule of the medical knowledge rule module, an evaluated treatment site result combination and priority order and a type and a dose of an injected filler.

Preferably, the personal facial feature contains a static texture feature, a static outline feature or a skin quality feature of an accustomed expression.

Preferably, before the AI aesthetic medicine identification and analysis process is performed, at least one of an artificial neural network algorithm and a deep learning algorithm is performed to train an artificial intelligence model of the AI aesthetic medicine identification and analysis process according to the plural aesthetic medical auxiliary evaluation results.

In accordance with a second embodiment of the present invention, an electronic device using the AI-assisted evaluation method of the present invention is provided. The electronic device at least includes an AI facial expression evaluation module, an AI aesthetic medicine identification and analysis module and an input/output module. The AI facial expression evaluation module provides the real-time facial expression evaluation result. The AI aesthetic medicine identification and analysis module performs the AI aesthetic medicine identification and analysis process. The AI aesthetic medicine identification and analysis module receives real-time facial expression evaluation result and generates the real-time aesthetic medicine auxiliary evaluation result. The input/output module outputs the real-time aesthetic medicine auxiliary evaluation result. The AI aesthetic medicine identification and analysis module receives at least one personal facial feature from at least one of the AI facial expression evaluation module and the input/output module.

Preferably, the electronic device is connected with at least one of the aesthetic medicine auxiliary evaluation result historical database and the medical knowledge rule module in at least one of a wireless transmission manner and a wired transmission manner.

Preferably, the electronic device is a handheld smart mobile device, a personal computer or a stand-alone smart device.

In accordance with a third embodiment of the present invention, an AI-assisted evaluation system for aesthetic medicine is provided. The AI-assisted evaluation system at least includes an AI facial expression evaluation module, an AI aesthetic medicine identification and analysis module and an input/output module. The AI facial expression evaluation module provides a real-time facial expression evaluation result of a subject. The AI aesthetic medicine identification and analysis module is connected with the AI facial expression evaluation module. The input/output module is connected with the AI aesthetic medicine identification and analysis module. After a basic data and/or a personal facial feature of the subject is inputted into the input/output module, the basic data and/or a personal facial feature of the subject is outputted to the AI aesthetic medicine identification and analysis module. The AI aesthetic medicine identification and analysis module receives at least one of the basic data and/or the personal facial feature of the subject and the real-time facial expression evaluation result. The AI aesthetic medicine identification and analysis module is connected with a medical knowledge rule module and an aesthetic medicine auxiliary evaluation result historical database. The AI aesthetic medicine identification and analysis module performs an AI aesthetic medicine identification and analysis process according to at least one of the medical knowledge rule module and the aesthetic medicine auxiliary evaluation result historical database, and adaptively generates and outputs a real-time aesthetic medicine auxiliary evaluation result.

Preferably, the AI aesthetic medicine identification and analysis module further feeds back and storing the real-time aesthetic medicine auxiliary evaluation result into the at least one of the medical knowledge rule module and the aesthetic medicine auxiliary evaluation result historical database.

Preferably, the real-time aesthetic medicine auxiliary evaluation result at least contains an evaluated treatment site result combination and priority order for the subject, or the real-time aesthetic medicine auxiliary evaluation result at least contains the evaluated treatment site result combination and priority order and a type and a dose of an injected filler.

Preferably, the medical knowledge rule module further includes a functional medical anatomy rule and a dynamic medical anatomy rule.

Preferably, the AI facial expression evaluation module includes an AI image detection unit, an AI image calibration and feature extraction unit, an AI facial action coding unit and an AI facial emotion recognition unit. The AI image detection unit performs an AI image detection process to acquire a real-time face image of the subject. The AI image calibration and feature extraction unit connected with the AI image detection unit. The AI image calibration and feature extraction unit performs an AI image calibration and feature extraction process according to the real-time face image, so that a facial surface and geometric feature information is acquired. The AI facial action coding unit is connected with the AI image calibration and feature extraction unit. The AI facial action coding unit performs an AI facial action coding process according to the facial surface and geometric feature information, so that plural pieces of facial action coding information are acquired. The AI facial emotion recognition unit is connected with the AI facial action coding unit. The AI facial emotion recognition unit performs an AI facial emotion recognition process according to the plural pieces of facial action coding information. Consequently, a proportional distribution and combination information of plural emotional indicators corresponding to the real-time face image is acquired and the real-time face image emotion evaluation result is generated.

Preferably, the AI image detection process is performed according to an AI machine learning method. The AI machine learning method includes a boundary detection algorithm corresponding to Haar-Like features in combination with an adaptive boosting machine learning method, or the AI machine learning method includes a histogram of oriented gradients (HOG) method in cooperation with a support vector machine (SVM) machine learning method.

Preferably, before the AI facial action coding process is performed, a machine learning method is performed to train a facial action coding model of the AI facial action coding process according to a specified number of training data sets and a facial action coding system (FACS).

Preferably, the facial action coding model is trained in different scenarios including a static expression scenario and/or a dynamic expression scenario, so that a static facial action coding information and a dynamic facial action coding information are respectively acquired.

Preferably, before the AI facial emotion recognition process is performed, another machine learning method is employed to train a facial emotion recognition model of the AI facial emotion recognition process according to at least one of an emotional valance, an emotional arousal and the plural emotional indicators in combination with the above facial action coding system.

Preferably, the AI image calibration and feature extraction unit includes a facial key point labelling unit, a facial calibration and masking unit and a facial feature extraction unit. The facial key point labelling unit is connected with the AI image detection unit. The facial key point labelling unit performs an AI facial key point labelling process to acquire a facial key point labelling information. The facial calibration and masking unit is connected with the facial key point labelling unit. The facial calibration and masking unit performs a facial image calibration process according to the facial key point labelling information, so that a normalized facial image information is acquired. The facial feature extraction unit connected with the facial calibration and masking unit. The facial feature extraction unit performs a facial image feature extraction process according to the facial key point labelling information and the normalized facial image information, so that the facial surface and geometric feature information is acquired.

Preferably, before the AI facial key point labelling process is performed, a machine learning method is performed to train a facial key point model of the AI facial key point labelling process according to a specified number of training data sets.

Preferably, the facial image feature extraction process at least includes a facial image surface feature extraction process and a facial image geometric feature extraction process. The facial image surface feature extraction process is performed through the histogram of oriented gradients (HOG) method to obtain multi-dimensional vector data, and a principal component analysis (PCA) technology is used to reduce a vector data amount and retain an important facial image surface feature information. The facial image feature geometric extraction process is performed to acquire a facial image geometric feature information according to the facial key point labelling information.

Preferably, the aesthetic medicine auxiliary evaluation result historical database contains plural aesthetic medical auxiliary evaluation results. Each of the plural aesthetic medical auxiliary evaluation results at least contains a subject name, a basic data, a historical face image emotion evaluation result, a personal facial feature, a functional medical anatomy rule and a dynamic medical anatomy rule of the medical knowledge rule module, an evaluated treatment site result combination and priority order and a type and a dose of an injected filler.

Preferably, the personal facial feature contains a static texture feature, a static outline feature or a skin quality feature of an accustomed expression.

Preferably, before the AI aesthetic medicine identification and analysis process is performed, at least one of an artificial neural network algorithm and a deep learning algorithm is performed to train an artificial intelligence model of the AI aesthetic medicine identification and analysis process according to the plural aesthetic medical auxiliary evaluation results.

Preferably, the AI facial expression evaluation module, the AI aesthetic medicine identification and analysis module and the input/output module are assembled as an electronic device. The electronic device is a handheld smart mobile device, a personal computer or a stand-alone smart device.

Preferably, the electronic device is connected with at least one of the aesthetic medicine auxiliary evaluation result historical database and the medical knowledge rule module in at least one of a wireless transmission manner and a wired transmission manner.

BRIEF DESCRIPTION OF THE DRAWINGS

FIG. 3 schematically illustrates the contents in the aesthetic medicine auxiliary evaluation result historical database as shown in FIG. 1.

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. In the following embodiments and drawings, the elements irrelevant to the concepts of the present invention are omitted and not shown.

Figure 1:
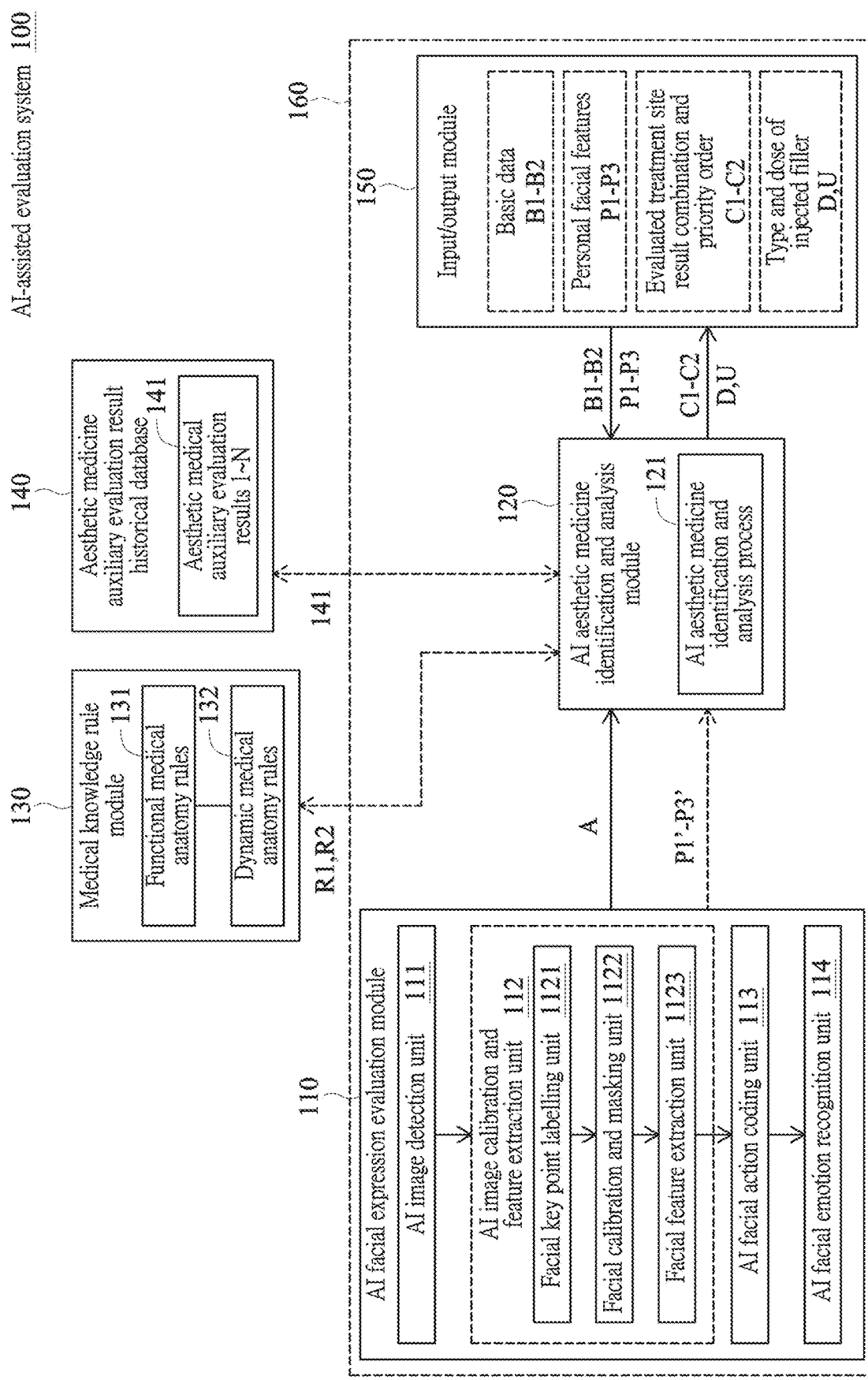
FIG. 1 is a schematic functional block diagram illustrating the concepts of an AI-assisted evaluation system according to an embodiment of the present invention.

FIG. 1 is a schematic functional block diagram illustrating the concepts of an AI-assisted evaluation system according to an embodiment of the present invention.

As shown in FIG. 1, the AI-assisted evaluation system of the present invention is based on facial expressions and applied to aesthetic medicine. The AI-assisted evaluation system 100 comprises an AI facial expression evaluation module 110, an AI aesthetic medicine identification and analysis module 120, a medical knowledge rule module 130, an aesthetic medicine auxiliary evaluation result historical database 140 and an input/output module 150.

The AI facial expression evaluation module 110 at least comprises an AI image detection unit 111, an AI image calibration and feature extraction unit 112, an AI facial action coding unit 113 and an AI facial emotion recognition unit 114. Preferably, the AI image calibration and feature extraction unit 112 comprises a facial key point labelling unit 1121, a facial calibration and masking unit 1122 and a facial feature extraction unit 1123.

The medical knowledge rule module 130 at least comprises a functional medical anatomy rule 131 and a dynamic medical anatomy rule 132. The functional medical anatomy rule 131 and the dynamic medical anatomy rule 132 include plural different medical rules R1 and R2, which will be described in FIG. 3.

The aesthetic medicine auxiliary evaluation result historical database 140 at least contains plural aesthetic medical auxiliary evaluation results 1~N (141). That is, the aesthetic medicine auxiliary evaluation result historical database 140 contains the aesthetic medical auxiliary evaluation results 1~N (141) corresponding to N historical records.

Moreover, the input/output module 150 is used to input or output various types of information. For example, the input/output module 150 receives and inputs the basic data B1~B2 and/or the personal facial features P1~P3 of the subject, and inputs them into the AI aesthetic medicine identification and analysis module 120. Alternatively, the input/output module 150 outputs a real-time aesthetic medicine auxiliary evaluation result that is received from the AI aesthetic medicine identification and analysis module 120. The input/output module 150 at least comprises evaluated treatment site result combination and priority orders C1~C2, the type D of an injected filler D and/or the dose U of the injected filler.

The basic data B1~B2 are related to the parameter information about the gender of the subject and the parameter information about the age of the subject, respectively. The personal facial features P1~P3 are related to the parameter information about the static texture feature P1, the parameter information about the static contour feature P2 and the parameter information about the skin quality feature P3 of the subject, respectively. The personal facial features P1'~P3' are directly provided by the AI facial expression evaluation module 110 and related to another parameter information about the facial features of the subject.

The basic data B1~B2 and/or the personal facial features P1~P3 (or P1'~P3') of the subject, the priority orders C1~C2, the type D of the injected filler D and/or the dose U of the injected filler, or the plural different medical rules R1 and R2 and the number and type of the parameter information associated with the aesthetic medicine auxiliary evaluation result are illustrated for explaining the aesthetic medicine auxiliary evaluation result historical database as shown in FIG. 3 later. It is noted that the number and type of the parameter information are not restricted.

In addition, the AI facial expression evaluation module 110, the AI aesthetic medicine identification and analysis module 120 and the input/output module 150 can be assembled as an electronic device 160. The electronic device 160 is a handheld smart mobile device, a personal computer (PC) or a stand-alone smart device. For example, the electronic device 160 is a tablet computer, a smart mobile device, a notebook computer, a desktop computer, a smart device that operates independently or a smart module that operates independently. The smart device or the smart module can be assembled in or separated from a medical device (not shown).

The electronic device 160 is connected with the aesthetic medicine auxiliary evaluation result historical database 140 and/or the medical knowledge rule module 130 in a wireless transmission manner and/or a wired transmission manner. For example, the aesthetic medicine auxiliary evaluation result historical database 140 and/or the medical knowledge rule module 130 are stored in a cloud storage platform, and the electronic device 160 is connected with the cloud storage platform through various local/wide area networks (not shown).

Please refer to FIG. 1 again. The AI facial expression evaluation module 110 is an important part of the technology of the present invention. Please also refer to FIGS. 2A-2E and FIG. 3. The AI image detection unit 111 is used to execute an AI image detection process. Moreover, after an image pickup operation is performed on the subject, for example a camera device (not shown) is used to photograph the subject, the AI image detection unit 111 acquires a real-time face image of the subject. The AI image calibration and feature extraction unit 112 is connected with the AI image detection unit 111. The AI image calibration and feature extraction unit 112 is used to perform an AI image calibration and feature extraction process according to the real-time face image, so that a facial surface and geometric feature information is acquired. The AI facial action coding unit 113 is connected with the AI image calibration and feature extraction unit 112. The AI facial action coding unit 113 is used to perform an AI facial action coding process according to the facial surface and geometric feature information, so that plural pieces of facial action coding information are acquired. The AI facial emotion recognition unit 114 is connected with the AI facial action coding unit 113. The AI facial emotion recognition unit 114 is used to perform an AI facial emotion recognition process according to the plural pieces of facial action coding information (e.g., the static facial action coding information AU1~AUn and the dynamic facial action coding information AU1'~AUn'). Consequently, a proportional distribution and combination information of plural emotional indicators (e.g., the emotional indicators A31~A33 as shown in FIG. 3) corresponding to the real-time face image is acquired and a real-time face image emotion evaluation result A is generated.

Moreover, an AI machine learning method can be applied to the AI image detection process. For example, Haar-Like features in combination with an adaptive boosting machine learning method is currently a popular and simple boundary detection algorithm for automatic face detection. In accordance with another detection algorithm, a histogram of oriented gradients (HOG) method in cooperation with a support vector machine (SVM) machine learning method is used. It is noted that the example of the AI machine learning method is not restricted.

Figure 2A:
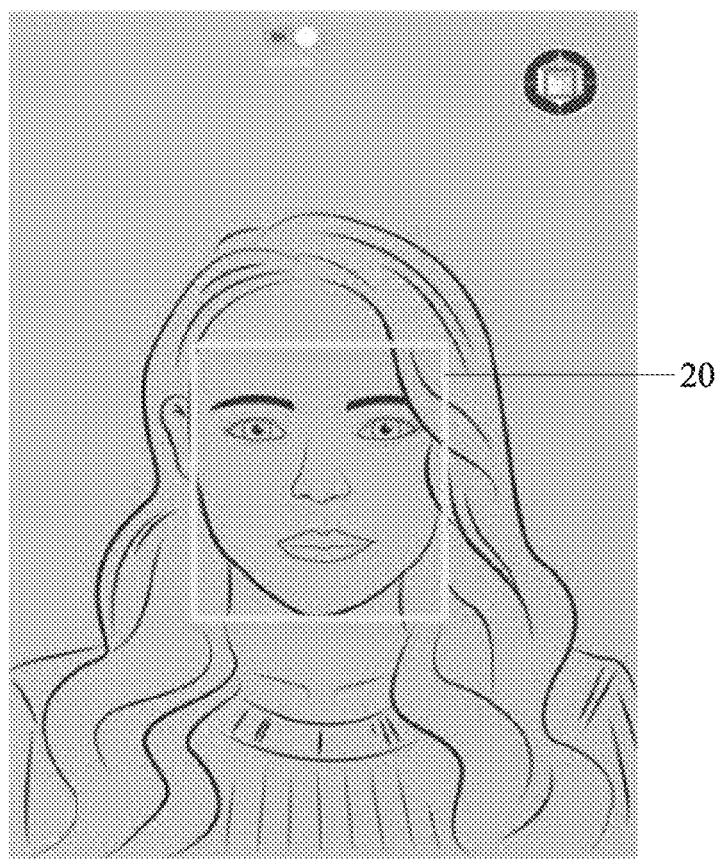
FIG. 2A is an implementation concept of the AI image detection unit as shown in FIG. 1.

FIG. 2A is an implementation concept of the AI image detection unit 111 as shown in FIG. 1. The detected face image is circumscribed with a rectangular (or square) frame 20. The circumscribed face image will be utilized by the AI image calibration and feature extraction unit 112 in the subsequent step.

Moreover, before the AI facial action coding process is performed, a machine learning method is used to train a facial action coding model of the AI facial action coding process according to a specified number of training data sets and a facial action coding system (FACS). For example, the facial action coding model is trained in different scenarios including a static expression scenario and/or a dynamic expression scenario. Consequently, a static facial action coding information (e.g., the static facial action coding information AU1~AUn as shown in FIG. 3) and a dynamic facial action coding information (e.g., the dynamic facial action coding information AU1'~AUn' as shown in FIG. 3) are respectively acquired.

In a preferred embodiment, when a new subject is tested, the AI facial action coding unit 113 of the AI facial expression evaluation module 110 requests that the new subject is tested in different scenarios including the static expression scenario and/or the dynamic expression scenario.

Consequently, the static facial action coding information AU1~AUn and the dynamic facial action coding information AU1'~AUn' of the new subject are also acquired. The information about the new subject is provided to the AI aesthetic medicine identification and analysis module 120 in order to achieve more precise identification and analysis. In addition, the information about the new subject can be stored into the aesthetic medicine auxiliary evaluation result historical database 140.

Figure 2B:
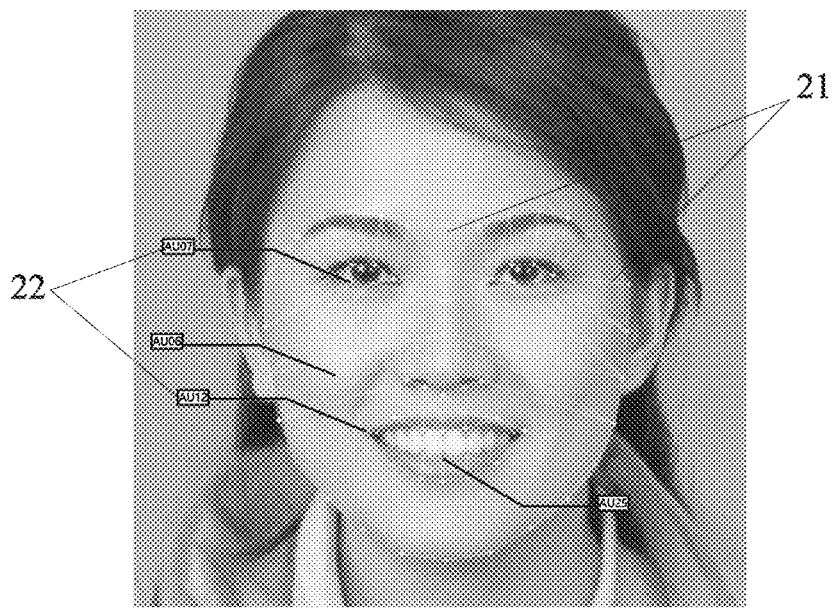
FIG. 2B is an implementation concept of the AI facial action coding unit as shown in FIG. 1 from the perspective of a facial key point labelling information.
Figure 2C:
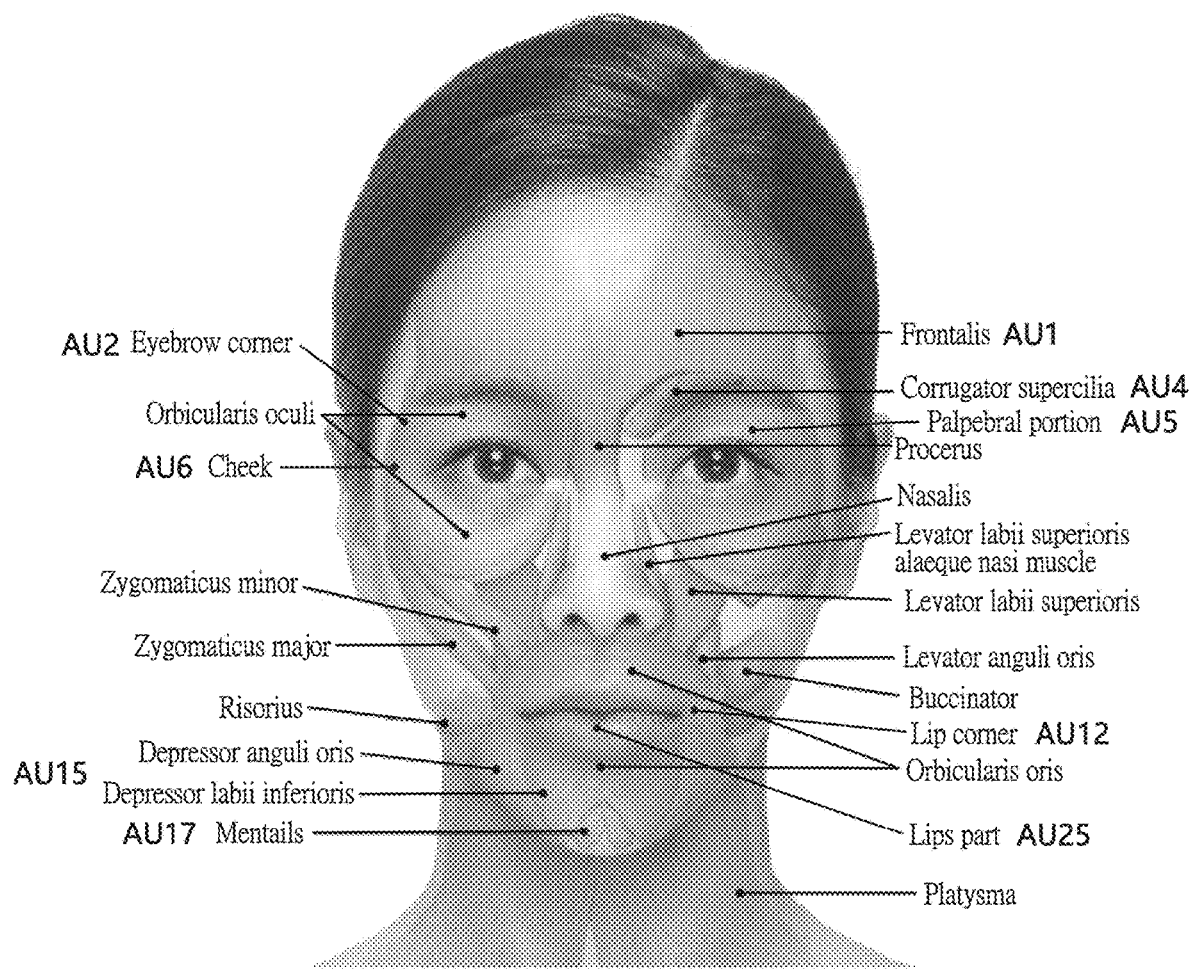
FIG. 2C is an implementation concept of the AI facial action coding unit as shown in FIG. 1 from the perspective of human anatomy.

FIG. 2B is an implementation concept of the AI facial action coding unit 113 as shown in FIG. 1 from the perspective of a facial key point labelling information. In this figure, the facial action coding information is a dynamic facial action coding information 21 representing a smiling face. FIG. 2C is an implementation concept of the AI facial action coding unit 113 as shown in FIG. 1 from the perspective of human anatomy.

As shown in FIG. 2C, the frown muscle at the brow is defined as the facial motion coding information AU4 (or Face Action Unit 4). In addition, the depressor anguli oris and the mentails, which may cause the lip corners to droop, are defined as the facial action coding information AU15 (or Face Action Unit 15) and the facial action coding information AU17 (or Face Action Unit 17), respectively.

Figure 2D:
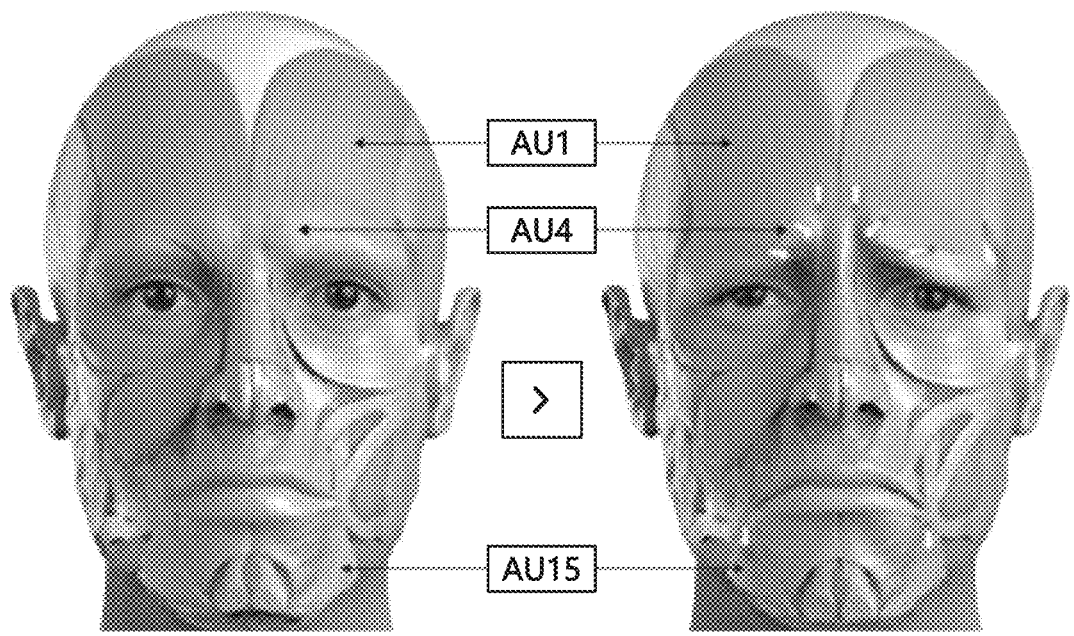
FIG. 2D is an implementation concept of using a machine learning method to train a facial action coding model in different scenarios including a static expression scenario and/or a dynamic expression scenario to acquire a static facial action coding information and a dynamic facial action coding information before the AI facial action coding unit as shown in FIG. 1 performs the AI facial action coding process.

FIG. 2D is an implementation concept of using a machine learning method to train a facial action coding model in different scenarios including a static expression scenario and/or a dynamic expression scenario to acquire a static facial action coding information and a dynamic facial action coding information before the AI facial action coding unit 113 as shown in FIG. 1 performs the AI facial action coding process.

The figure at the left side of FIG. 2D is used to observe plural pieces of static facial action coding information of the subject (e.g., AU1, AU4, AU15) in a static state or in a face-relaxed state when a short video is recorded. This figure is used to detect and analyze the situations of the related specific facial muscle groups of the subject in the static state and to observe whether forces or motions are unconsciously applied in a static state. Moreover, the figure at the right side of FIG. 2D is used to observe plural pieces of dynamic facial action coding information of the subject (e.g., AU1', AU4', AU15', not shown in the figure). According to different emotions, different facial expressions can be dynamically presented. For example, these emotions include sad emotions or more other angry emotions, laughing emotions, and so on. In addition, the dynamic changes of the related specific facial muscle groups can be observed accordingly.

In another embodiment, before the AI facial emotion recognition process is performed, another machine learning method is used to train a facial emotion recognition model of the AI facial emotion recognition process according to at least one of an emotional valance, an emotional arousal and some parameters (e.g., the emotional indicators A31~A33 of FIG. 3) in combination with the above facial action coding system (FACS).

Figure 2E:
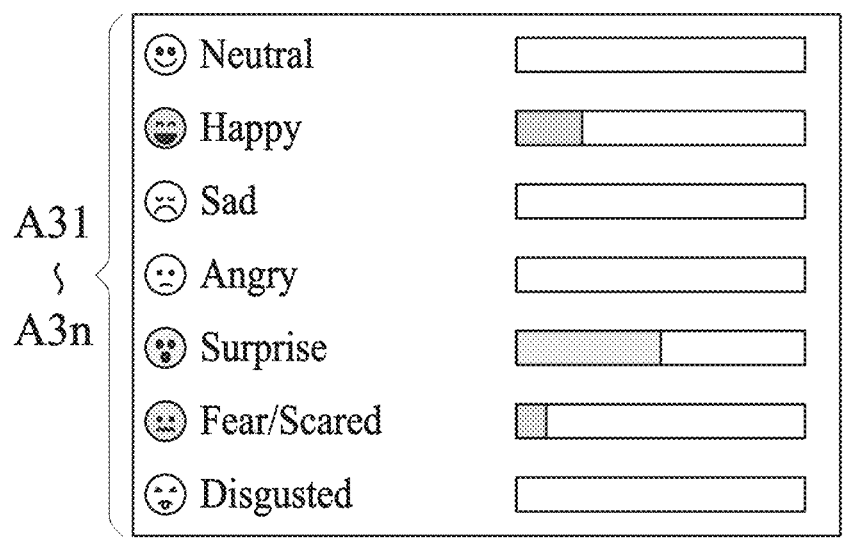
FIG. 2E is an implementation concept of the AI facial emotion recognition unit as shown in FIG. 1 in combination with emotion theories to quantitatively analyze the action strength of the facial muscle groups corresponding to each facial action coding information.

FIG. 2E is an implementation concept of the AI facial emotion recognition unit 114 as shown in FIG. 1 in combination with emotion theories to quantitatively analyze the action strength of the facial muscle groups corresponding to each facial action coding information. For example, the facial emotion expressions are classified into 7 categories of definitions by the AI facial expression evaluation module 110. In addition to the neutral expression, the other 6 expressions include the happy expression, the sad expression, the angry expression, the surprise expression, the fear/scared expression and the disgusted expression. Consequently, various emotional indicators are formed according to these facial emotion expressions. It is noted that the examples of the facial emotion expressions are not restricted.

The emotion theories that can be applied to and combined with the AI facial emotion recognition process at least comprise the "Dimensional Theories of Emotion" proposed by Lisa Feldman Barrett or the "Discrete Theories of Emotion" proposed by Paul Ekman. It is noted that the examples of the emotion theories are not restricted.

As mentioned above, the AI image calibration and feature extraction unit 112 comprises the facial key point labelling unit 1121, the facial calibration and masking unit 1122 and the facial feature extraction unit 1123. The facial key point labelling unit 1121 is connected with the AI image detection unit 111. The facial key point labelling unit 1121 performs an AI facial key point labelling process to acquire a facial key point labelling information. The facial calibration and masking unit 1122 is connected with the facial key point labelling unit 1121. The facial calibration and masking unit 1122 performs a facial image calibration process according to the facial key point labelling information, so that a normalized facial image information is acquired. The facial feature extraction unit 1123 is connected with the facial calibration and masking unit 1122. The facial feature extraction unit 1123 performs a facial image feature extraction process according to the facial key point labelling information and the normalized facial image information, so that the facial surface and geometric feature information is acquired.

Preferably, before the AI facial key point labelling process is performed, a machine learning method is used to train a facial key point model of the AI facial key point labelling process according to a specified number of training data sets. Preferably, in the facial image calibration process, at least an affine transformation technology is used to eliminate errors caused by different postures in the facial key point labelling information and unify size and presentation of the face image, so that the normalized facial image information is acquired.

In another embodiment, the facial image feature extraction process at least comprises a facial image surface feature extraction process and a facial image geometric feature extraction process. The facial image surface feature extraction process can be performed through the histogram of oriented gradients (HOG) method to obtain multi-dimensional vector data, and a principal component analysis (PCA) technology is used to reduce the vector data amount and retain the important facial image surface feature information. The facial image feature geometric extraction process is performed to acquire the facial image geometric feature information according to the facial key point labelling information.

Please refer to FIG. 1 again. Preferably but not exclusively, before the AI aesthetic medicine identification and analysis module 120 performs the AI aesthetic medicine identification and analysis process, at least one of an artificial neural network algorithm and a deep learning algorithm is used to train the artificial intelligence model of the AI aesthetic medicine identification and analysis process according to the aesthetic medical auxiliary evaluation results 1~N (141).

As shown in FIG. 3, the aesthetic medicine auxiliary evaluation result historical database 140 contains the plural aesthetic medical auxiliary evaluation results 1~N (141). Each aesthetic medical auxiliary evaluation result at least contains a subject name, a basic data B, a historical face image emotion evaluation result A', a personal facial feature P, a functional medical anatomy rule 131 and a dynamic medical anatomy rule 132 of the medical knowledge rule module 130 (R1, R2), the evaluated treatment site result combination and priority orders C1~C2, and the type D and the dose U of the injected filler.

In an embodiment, the basic data B contains the gender B1 and the age B2. The historical face image emotion evaluation result A' at least contains a static facial action coding information combination A1, a dynamic facial action coding information combination A2 and plural emotional indicators A31~A33. The static facial action coding information combination A1 contains the static state parameter values of plural pieces of static facial action coding information AU1~AUn of the subject without any emotion. The dynamic facial action coding information combination A2 contains the dynamic state parameter values of plural pieces of dynamic facial action coding information AU1'~AUn' of the subject according to different emotions. In an embodiment, the emotional indicators A31~A33 are negative emotional indicators. For example, A31 is a fear indicator, A32 is an angry indicator, and A33 is a contempt indicator. In another embodiment, the emotional indicators A31~A33 are positive emotional indicators. For example, A31 is a happy indicator, A32 is a moving indicator, and A33 is a satisfaction indicator.

The personal facial feature P contains the static texture feature P1, the static outline feature P2 or the skin quality feature P3 of the accustomed expression. The personal facial features P1~P3 are provided by at least one of the AI facial expression evaluation module 110 and the input/output module 150.

For example, the medical rule R1 of the functional medical anatomy rule 131 contains the stretching level rules and the tension level rules R11~R14 of various facial muscle group in response to different emotional expressions. For example, the medical rule R2 of the dynamic medical anatomy rule 132 contains the linkage rules and the shrinkage rules R21~R24 between various facial muscle groups in response to different emotional expressions.

For example, the evaluated treatment site result combination and priority orders C1~C2 comprise one of plural pieces of static facial action coding information AU1~AUn and plural pieces of dynamic facial action coding information AU1'~AUn', or the combination thereof. The type D of the injected filler contains a hydrogel type W, a Botulinum toxin type X, a hyaluronic acid type Y and a collagen type Z. The use of the hydrogel type W, the hyaluronic acid type Y and the collagen type Z can reduce the static texture of the facial expression and thus reduce the combination of negative emotional indicators (e.g., the sad indicator and the angry indicator). In addition, the use of the hydrogel type W, the hyaluronic acid type Y and the collagen type Z can increase the combination of the positive emotional indicators (e.g., the happy indicator and the satisfaction indicator).

It is noted that the contents of the aesthetic medical auxiliary evaluation results 1~N (141) may be varied according to the practical requirements. That is, the contents of the aesthetic medical auxiliary evaluation results 1~N (141) may be modified or designed by those skilled in the art or adjusted according to the requirements of aesthetic medicine.

Figure 4:
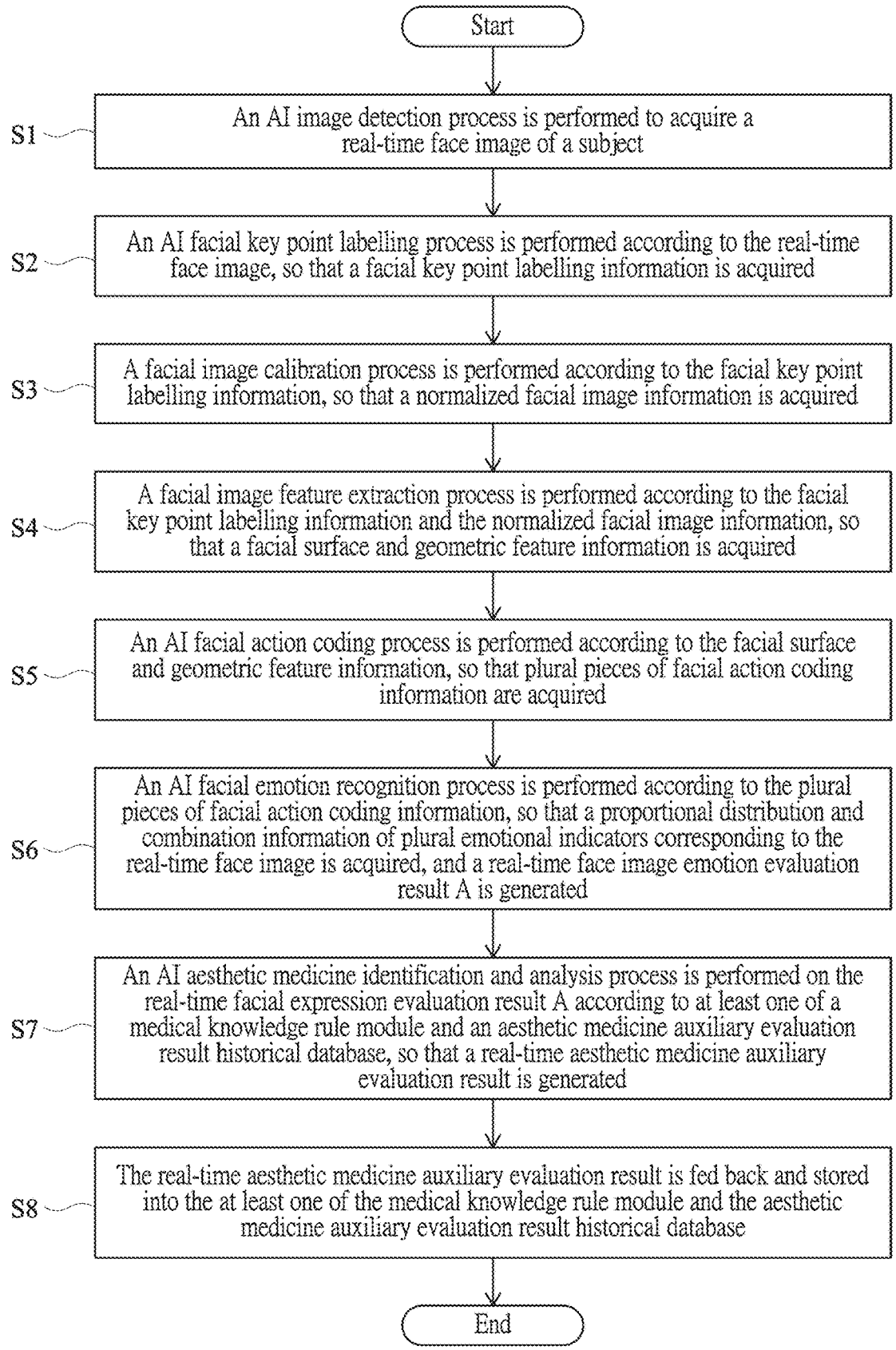
FIG. 4 is a flowchart illustrating the concepts of an AI-assisted evaluation method for aesthetic medicine according to an embodiment of the present invention.

FIG. 4 is a flowchart illustrating the concepts of an AI-assisted evaluation method for aesthetic medicine according to an embodiment of the present invention. Please refer to FIG. 4 and also refer to FIGS. 1, 2 and 3. The AI-assisted evaluation method at least comprises the following steps.

Firstly, the flowchart of the AI-assisted evaluation method is started.

In a step S1, an AI image detection process is performed to acquire a real-time face image of a subject.

In a step S2, an AI facial key point labelling process is performed according to the real-time face image, so that a facial key point labelling information is acquired.

In a step S3, a facial image calibration process is performed according to the facial key point labelling information, so that a normalized facial image information is acquired.

In a step S4, a facial image feature extraction process is performed according to the facial key point labelling information and the normalized facial image information, so that a facial surface and geometric feature information is acquired;

In a step S5, an AI facial action coding process is performed according to the facial surface and geometric feature information, so that plural pieces of facial action coding information are acquired.

In a step S6, an AI facial emotion recognition process is performed according to the plural pieces of facial action coding information. Consequently, a proportional distribution and combination information of plural emotional indicators corresponding to the real-time face image is acquired, and a real-time face image emotion evaluation result A is generated.

In a step S7, an AI aesthetic medicine identification and analysis process is performed on the real-time facial expression evaluation result A according to at least one of a medical knowledge rule module and an aesthetic medicine auxiliary evaluation result historical database, so that a real-time aesthetic medicine auxiliary evaluation result is generated.

In a step S8, the real-time aesthetic medicine auxiliary evaluation result is fed back and stored into the at least one of the medical knowledge rule module and the aesthetic medicine auxiliary evaluation result historical database.

Then, the flowchart is ended.

Hereinafter, some implementation concepts will be provided to describe how to perform the aesthetic medicine behaviors through the AI-assisted evaluation method and the AI-assisted evaluation system of the present invention. In the following embodiments, the main treatment target requirements are related to the improvements of the negative emotional indicator combinations of the subject 1, the subject 2 and the subject 3. Moreover, the reduction or improvement of the negative emotional indicator combination in response to the negative emotions is helpful to enhance personal attractiveness and interpersonal relationships.

For example, the main therapeutic purpose of these preferred embodiments is to reduce or improve involuntary frowning or drooping facial expressions to reduce the feeling of being angry or serious, and even reduce negative micro-expressions. In other embodiments, the part of the positive emotional indicator combination is further strengthened. Consequently, higher-quality, more accurate and personalized aesthetic therapeutic effects can be achieved.

FIGS. 5A to 5F schematically illustrate a first implementation example of the aesthetic medicine using the AI-assisted evaluation method and the AI-assisted evaluation system of the present invention.

Please refer to the contents of FIGS. 5A to 5F and also the contents of FIGS. 1 to 4. By the AI facial expression evaluation module 110, plural pieces of static facial action coding information AU1~AUn of the subject 1 are detected, and plural pieces of dynamic facial action coding information AU1'~AUn' (not shown) are acquired according to the expression change between a detection result of each static facial action coding information AU1~AUn and another detection result of another static facial action coding information AU1~AUn. Consequently, a real-time facial expression evaluation result A is generated. The real-time facial expression evaluation result A is formed according to the combination of the proportional results of the emotion indicates, and the emotion indicates are generated according to the information static facial action coding information combination A1 and the dynamic facial action coding information combination A2.

Figure 5A:
FIGS. 5A to 5F schematically illustrate a first implementation example of the aesthetic medicine using the AI-assisted evaluation method and the AI-assisted evaluation system of the present invention.

Please refer to FIG. 5A. The subject may frown unconsciously, or the lip corners of the subject may droop because of aging. The micro-expressions caused by the plural pieces of static facial action coding information AU1~AUn are recorded and synthesized as the static facial motion coding information combination A1.

Figure 5B:
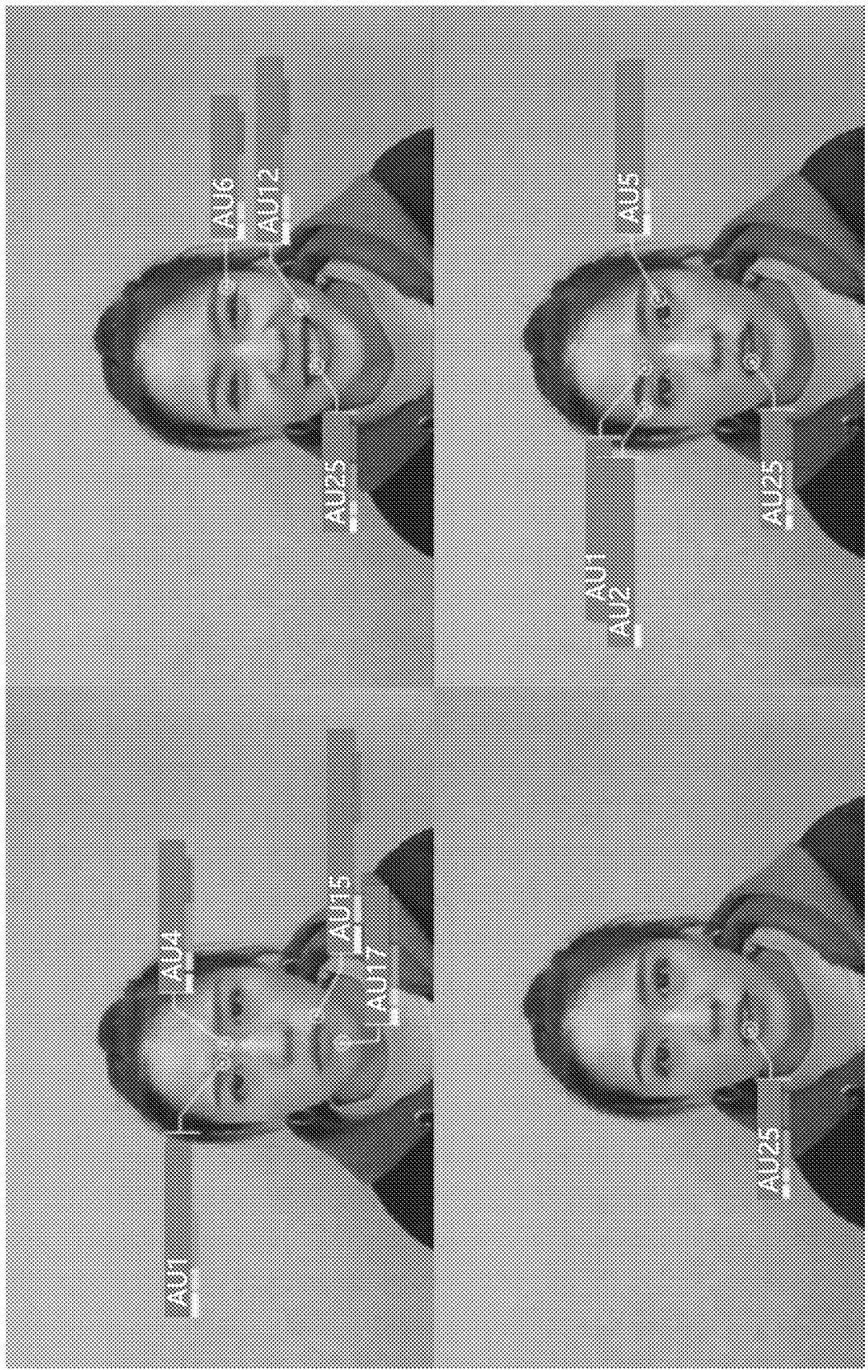

Please refer to FIG. 5B. The dynamic facial action coding information combination A2 is the combination of different facial expressions of the subject 1 in response to different emotions. For example, the facial expressions include the angry expression, the laughing expression, and so on.

Then, the AI facial emotion recognition unit 114 further quantitatively analyzes the action strength of the facial muscle group corresponding to each facial action coding information in different emotional expressions (including the static facial motion coding information combination A1 and the dynamic facial action coding information combination A2). Consequently, more accurate dynamic parameter values are provided as the treatment references for the emotional indicators A31~A33, the evaluated treatment site result combination and priority orders C1~C2, the type D of the injected filler and the dose U of the injected filler.

Figures 5C, 5D:
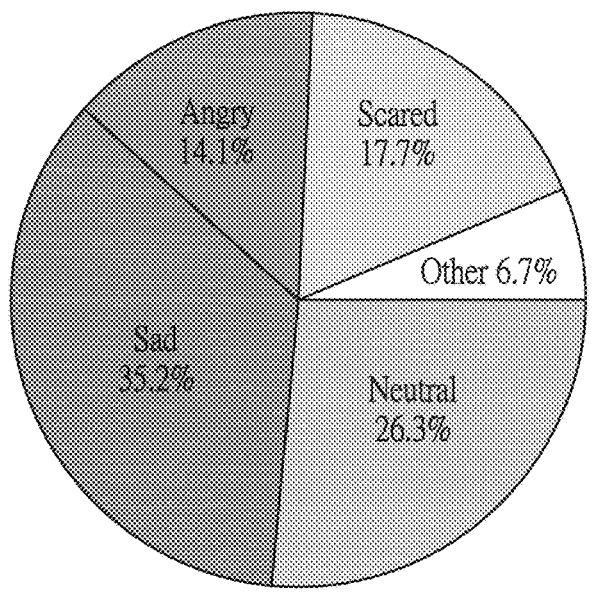

Please refer to FIGS. 5C and 5D. The plural emotional indicators A31~A33 of the subject 1 represent the sad indictor of 35.2%, the angry indicator of 14.1% and the scared indicator of 17.7%, respectively. In addition, the plural pieces of static facial action coding information AU1~AUn corresponding to the emotional indicators A31~A33 are also shown.

Moreover, the AI facial expression evaluation module 110 may cooperate with a facial three-dimensional (3D) simulation unit and a skin quality detection unit to provide the static texture feature P1, the static outline feature P2 or the skin quality feature P3 of the accustomed expression (not shown).

Figure 5E:
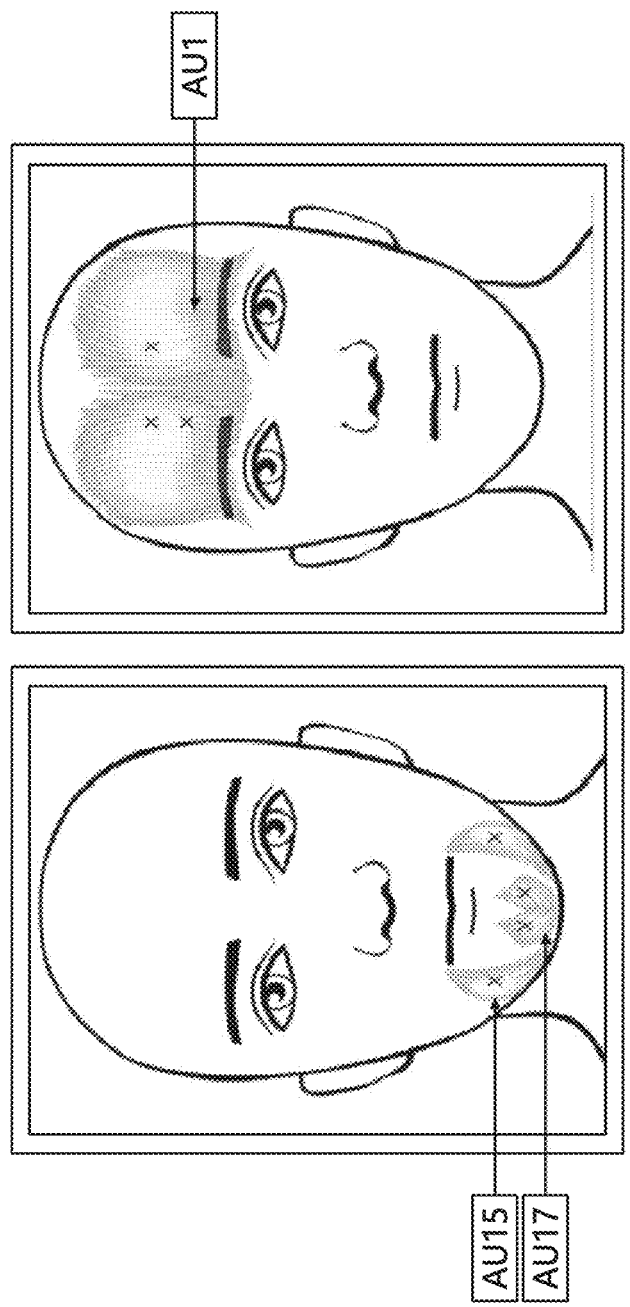

Please refer to FIG. 5E. Then, the real-time facial expression evaluation result A is inputted into the AI aesthetic medicine identification and analysis module 120, or the AI aesthetic medicine identification and analysis module 120 actively receives the real-time facial expression evaluation result A. In addition, the AI aesthetic medicine identification and analysis module 120 cooperates with one of the medical knowledge rule module 130 and the aesthetic medicine auxiliary evaluation result historical database 140 to perform an AI aesthetic medicine identification and analysis process 121. Then, a real-time aesthetic medicine auxiliary evaluation result of the subject 1 is generated and outputted. The real-time aesthetic medicine auxiliary evaluation result at least contains the evaluated treatment site result combination and priority orders C1~C2, the type D of the injected filler and the dose U of the injected filler.

In this embodiment, the advice on the aesthetic medicine auxiliary evaluation result is given as follows. For example, the muscle group related to the facial motion coding information AU1 (e.g., inner frontalis) was administered with Botulinum Toxin 8 s.U, and the muscle group related to the facial motion coding information AU15 (e.g., depressor anguli oris) and the muscle group related to the facial motion coding information AU17 (e.g., mentails) were respectively administered with Botulinum Toxin DAO 4 s.U. and Botulinum Toxin Mentalis 4 s.U.

Figure 5F:
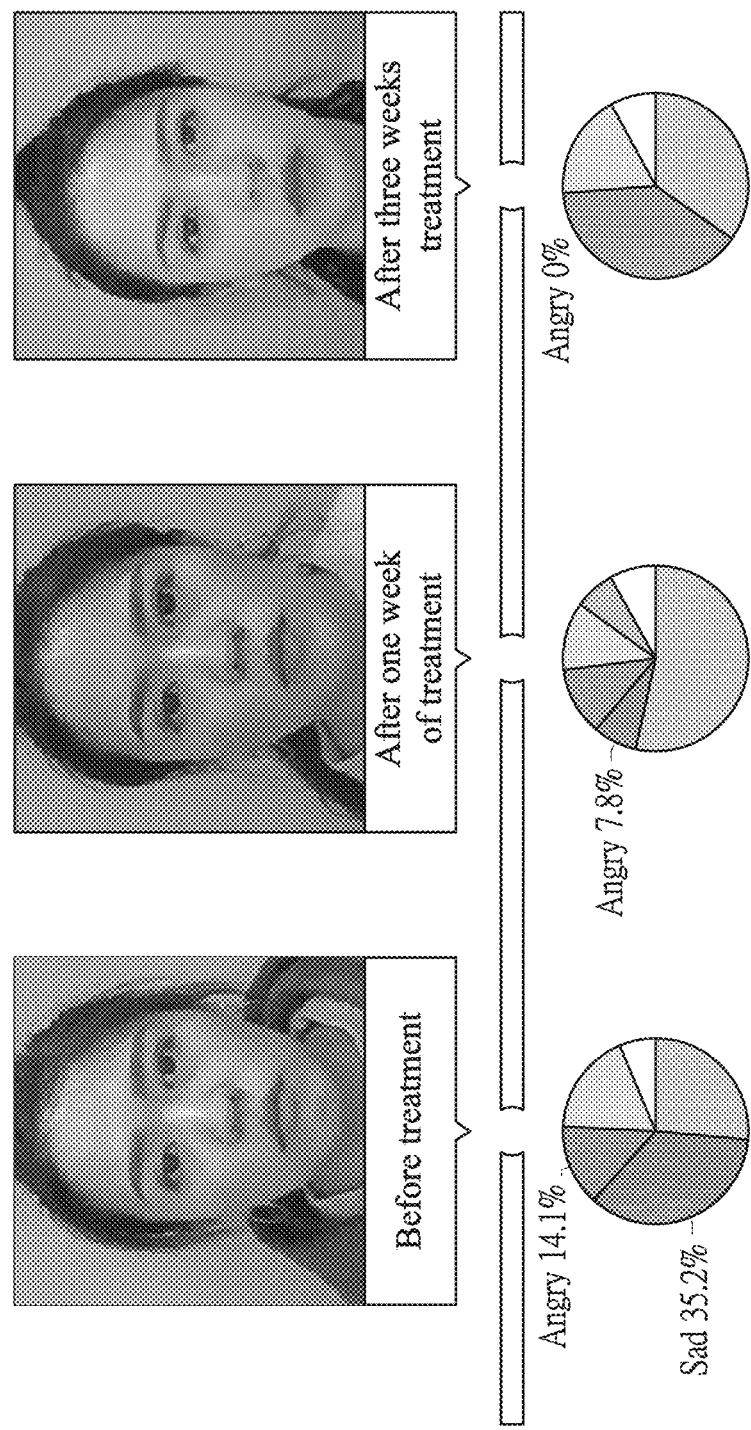

Please refer to FIG. 5F. The aesthetic therapeutic effects can be assessed by comparing the real-time facial expression evaluation results of the subject 1 before the treatment, one week after the treatment and three weeks after the treatment. It can be found that the sad indicator of the face of the subject 1 was directly reduced from 35.2% to 0% after one week of treatment. In addition, the angry indicator of the subject 1 was reduced from 14.1% (before treatment) to 7.8% after one week of treatment. Especially, even after three weeks of Botulinum Toxin treatment, the sad indicator of the face was completely reduced to 0%.

In this embodiment, the advice on the aesthetic medicine auxiliary evaluation result corresponding to the sad indicator and another treatment reference guide are given as follows. For example, if the sad indicator accounts for more than 10% of the total emotional indicator combination (i.e., the total expression) and the facial motion coding information AU1, the facial motion coding information AU4 and the facial motion coding information AU15 are all strengthen (i.e., the percentages are increased), it is recommended to inject Botulinum Toxin A type into the corresponding muscle group. It is noted that the example of the aesthetic medicine auxiliary evaluation result is not restricted. For example, more case data (i.e., the aesthetic medicine auxiliary evaluation results) and multiple AI deep learning/training procedures can be used to obviously propose better treatment recommendations.

Figure 6:
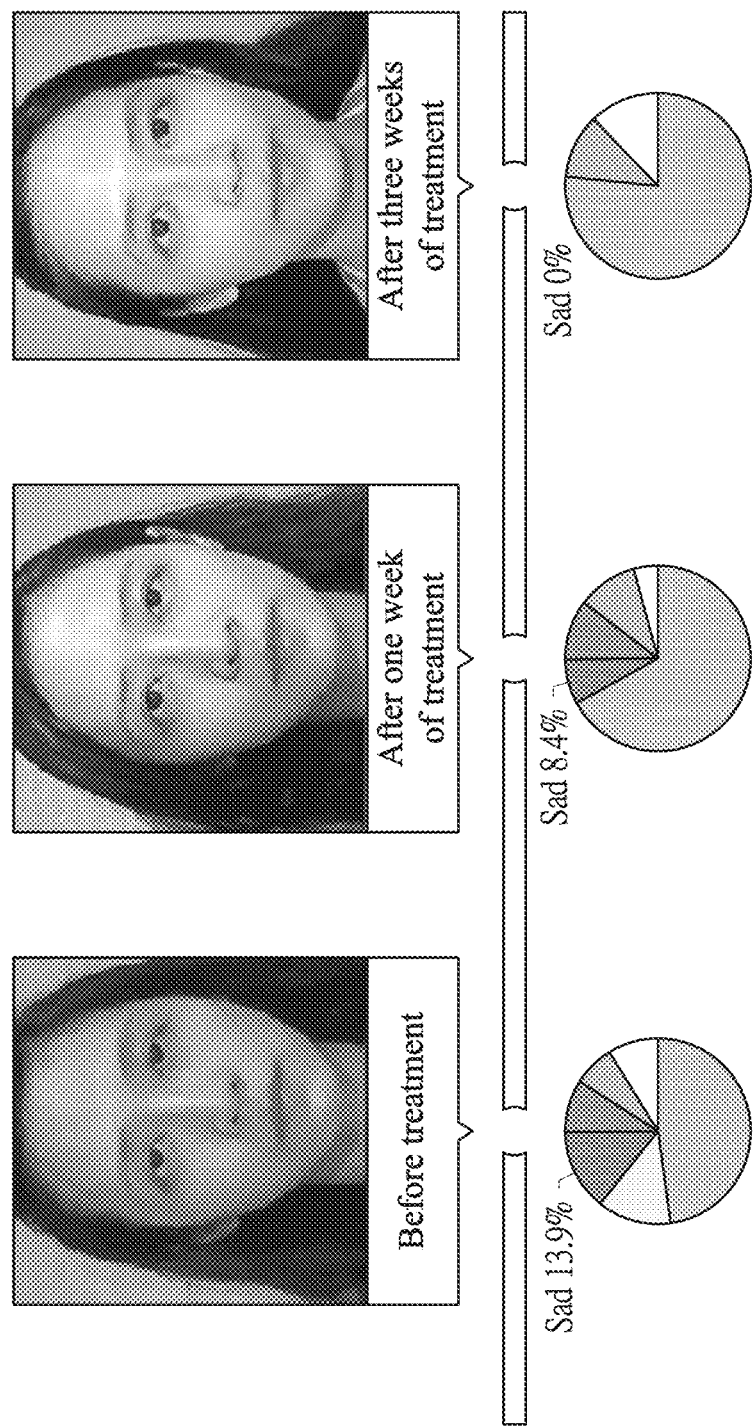
FIG. 6 schematically illustrates a second implementation example of the aesthetic medicine using the AI-assisted evaluation method and the AI-assisted evaluation system of the present invention.

FIG. 6 schematically illustrates a second implementation example of the aesthetic medicine using the AI-assisted evaluation method and the AI-assisted evaluation system of the present invention.

Please refer to FIG. 6. By the AI facial expression evaluation module 110, plural pieces of static facial action coding information AU1~AUn and plural pieces of dynamic facial action coding information AU1'~AUn' (not shown) of the subject 2 are detected. Consequently, a real-time facial expression evaluation result A is generated. Among plural emotional indicators of the subject 2, the neutral indicator (26.3%) is the highest, and the sad indicator (13.9%) is the second highest. In the aesthetic medicine auxiliary evaluation result, the site having the highest priority to be subjected to the treatment is related to the facial motion coding information AU1 that mainly leads to the sad indicator and is contributed to inner brow raiser.

Accordingly, the real-time facial expression evaluation result A can be combined with the medical knowledge rule module 130 and the aesthetic medicine auxiliary evaluation result historical database 140. That is, the uses of the functional medical anatomy rule and the dynamic medical anatomy rule can point out the locations of the muscle groups that are highly correlated and linked with the aforementioned facial motion coding information AU1. Then, the advice on the real-time aesthetic medicine auxiliary evaluation result for personalized aesthetic medicine is given as follows. For example, the muscle group related to the facial motion coding information AU1 (e.g., inner frontalis) was administered with Botulinum Toxin 8 s.U.

The aesthetic therapeutic effects can be assessed by comparing the real-time facial expression evaluation results of the subject 2 before the treatment, one week after the treatment and three weeks after the treatment. It can be found that the sad indicator of the face of the subject 2 was directly reduced from 13.9% to 8.4% after one week of treatment. Especially, even after three weeks of Botulinum Toxin treatment, the sad indicator of the face was completely reduced to 0%. In other words, the aesthetic therapeutic effects of the AI-assisted evaluation method and the AI-assisted evaluation system for aesthetic medicine are really remarkable.

Figure 7:
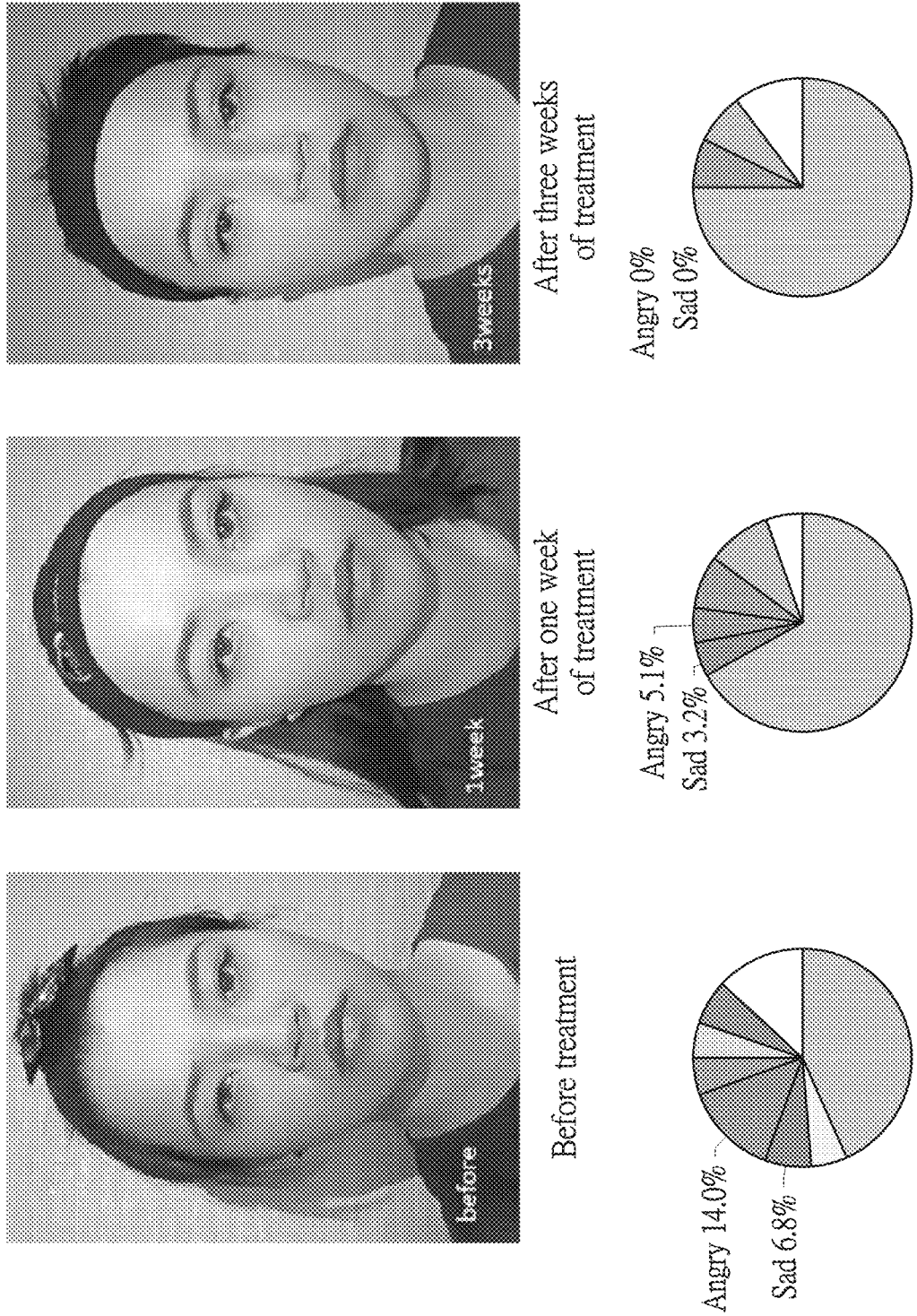
FIG. 7 schematically illustrates a third implementation example of the aesthetic medicine using the AI-assisted evaluation method and the AI-assisted evaluation system of the present invention.

FIG. 7 schematically illustrates a third implementation example of the aesthetic medicine using the AI-assisted evaluation method and the AI-assisted evaluation system of the present invention.

Please refer to FIG. 7. By the AI facial expression evaluation module 110, plural pieces of static facial action coding information AU1~AUn and plural pieces of dynamic facial action coding information AU1'~AUn' (not shown) of the subject 3 are detected. Consequently, a real-time facial expression evaluation result A is generated. Regardless of the genders or ages, the human angry expressions are generally related to the muscle groups of the aforementioned facial motion coding information AU15 and facial motion coding information AU17. The aesthetic therapeutic effects can be assessed by comparing the real-time facial expression evaluation results of the subject 3 before the treatment, one week after the treatment and three weeks after the treatment. It can be found that the angry indicator of the face of the subject 3 has considerable improvement after three weeks of treatment.

In this embodiment, the advice on the aesthetic medicine auxiliary evaluation result corresponding to the angry indicator and another treatment reference guide are given as follows. For example, if the angry indicator accounts for more than 10% of the total emotional indicator combination and the facial motion coding information AU15 and the facial motion coding information AU17 are both strengthen (i.e., the percentages are increased), it is recommended to inject Botulinum Toxin A type into the corresponding muscle group (e.g., the depressor anguli oris and the mentails).

After the above embodiments are compared with the conventional technology of providing the aesthetic medical treatment recommendations according to the personal judgment of doctors only, it can be found that the conventional method is easily limited by the influence of doctors' personal experiences and stereotypes. Since the conventional method cannot be considered in a comprehensive and objective manner, the drawback of missing the differences in the micro-expressions of each person occur.

For example, in case that the goal of treatment is to reduce the angry indicator, doctors often use botulinum toxin to reduce the movement of the frown muscles but ignore the fact that the muscle movement of each person's angry expression is slightly different. A few persons may have the lip corners droop, or the jaw muscles may contract and arise. There are also some actions on the inner side of the eyebrow lift muscles. In addition, the movement of these muscles may only be partially visible to the naked eyes. Since the muscle movement is too subtle and difficult to be detected, blind spots and misunderstandings in treatment are readily generated. Under this circumstance, the adverse therapeutic effects and unnecessary medical disputes occur.

Firstly, if the main treatment sites of the subject 1 in the example of FIGS. 5A to 5F are related to the facial action coding information AU15 and the facial action coding information AU17 according to the aesthetic medical treatment recommendation of the personal judgment of the doctor, the facial action coding information AU1 corresponding to the angry indicator is missed by the doctor. Consequently, the therapeutic effect of the aesthetic medical treatment is not satisfied (not shown).

Secondly, the main treatment site of the subject 2 in the example of FIG. 6 is usually related to the facial action coding information AU2 according to the aesthetic medical treatment recommendation of the personal judgment of the doctor. The judgment is based on the fact that the orbicularis oculi muscle of the subject 2 causes the eyes to droop and leads to the sad indicator. After the aesthetic medical treatment is carried out, the aesthetic therapeutic effects can be assessed by comparing the real-time facial expression evaluation results of the subject 2 before the treatment, one week after the treatment and three weeks after the treatment. It can be found that the sad indicator of the face of the subject 2 was directly reduced from 6.8% to 5.1% after one week of treatment. However, after three weeks of Botulinum Toxin treatment, the sad indicator returned to 6.7%. The reason is that the doctor wrongly judges the treatment site of the subject 2. Consequently, the therapeutic effect of the aesthetic medical treatment is not satisfied, and the sad indicator is unable to be effectively improved (not shown).

Secondly, the main treatment site of the subject 3 in the example of FIG. 7 is usually related to the facial action coding information AU17 and the treatment site is administered with 4 units of abobotulinumtoxin A according to the aesthetic medical treatment recommendation of the personal judgment of the doctor. After the aesthetic medical treatment is carried out, the aesthetic therapeutic effects can be assessed by comparing the real-time facial expression evaluation results of the subject 3 before the treatment, one week after the treatment and three weeks after the treatment. It can be found that the angry indicator of the face of the subject 3 was directly reduced from 10.9% to 5.9% after one week of treatment. However, after three weeks of abobotulinumtoxin treatment, the angry indicator increased to 13.9%. The reason is that the doctor wrongly judges the treatment site of the subject 3 (e.g., the facial action coding information AU15) and the dose of abobotulinumtoxin A injected into the treatment site corresponding to the facial action coding information AU17 is insufficient. Consequently, instead of improving the subject's facial expression, the opposite effect of increasing the angry indicator is generated.

From the above descriptions, the present invention provides the AI-assisted evaluation method for aesthetic medicine and the evaluation system using the AI-assisted evaluation method. The AI facial expression evaluation module 110 provides the high-quality real-time facial expression evaluation result A of the subject. In addition, the AI aesthetic medicine identification and analysis module 120 optionally cooperates with the plural medical rules of the medical knowledge rule module and the aesthetic medicine auxiliary evaluation result historical database to perform the AI aesthetic medicine identification and analysis process. Consequently, the aesthetic medicine auxiliary evaluation result is generated and outputted. The aesthetic medicine auxiliary evaluation result at least contains the evaluated treatment site result combination and priority order of the subject and/or a type and a dose of an injected filler. Consequently, the technology of the present invention can not only accurately analyze and evaluate the correct and complete treatment site, but also accurately provide the type and dose of injected filler. In this way, the personalized aesthetic therapeutic effect can be achieved.

Moreover, the technology of the present invention can be used to carry out the aesthetic medicine behaviors to strengthen the combination of the positive emotional indicators. Alternatively, the technology of the present invention can be used to provide aesthetic medical treatment recommendation for preventive improvement on the facial aging treatment sites. For example, the relaxation of the facial muscles may cause the lip corners to droop, and thus the facial expression with the angry indicator is generated.

Moreover, the method and the system of the present invention can be applied to aesthetic medicine or aesthetic applications. The method and the system of the present invention can also be used as a basis for judging the therapeutic effect before and after the aesthetic medical surgery. The method and the system of the present invention can be used in the field of medical teachings to train doctors to further study or improve blind spots and misunderstandings in previous treatments.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

The invention claimed is:

1. An AI-assisted evaluation system for aesthetic medicine, the AI-assisted evaluation system at least comprises:
    an AI facial expression evaluation module providing a real-time facial expression evaluation result of a subject;
    an AI aesthetic medicine identification and analysis module connected with the AI facial expression evaluation module; and
    an input/output module connected with the AI aesthetic medicine identification and analysis module, wherein after a basic data and/or a personal facial feature of the subject is inputted into the input/output module, the basic data and/or a personal facial feature of the subject is outputted to the AI aesthetic medicine identification and analysis module,
    wherein the AI aesthetic medicine identification and analysis module receives at least one of the basic data and/or the personal facial feature of the subject and the real-time facial expression evaluation result, and the AI aesthetic medicine identification and analysis module is connected with a medical knowledge rule module and an aesthetic medicine auxiliary evaluation result historical database, wherein the AI aesthetic medicine identification and analysis module performs an AI aesthetic medicine identification and analysis process according to at least one of the medical knowledge rule module and the aesthetic medicine auxiliary evaluation result historical database, and adaptively generates and outputs a real-time aesthetic medicine auxiliary evaluation result;
    wherein the AI facial expression evaluation module comprises:
        an AI image detection unit performing an AI image detection process to acquire a real-time face image of the subject;
        an AI image calibration and feature extraction unit connected with the AI image detection unit, wherein the AI image calibration and feature extraction unit performs an AI image calibration and feature extraction process according to the real-time face image, so that a facial surface and geometric feature information is acquired;
        an AI facial action coding unit connected with the AI image calibration and feature extraction unit, wherein the AI facial action coding unit performs an AI facial action coding process according to the facial surface and geometric feature information, so that plural pieces of facial action coding information are acquired; and an AI facial emotion recognition unit connected with the AI facial action coding unit, wherein the AI facial emotion recognition unit performs an AI facial emotion recognition process according to the plural pieces of facial action coding information, so that a proportional distribution and combination information of plural emotional indicators corresponding to the real-time face image is acquired and the real-time face image emotion evaluation result is generated.

2. The AI-assisted evaluation system according to claim 1, wherein the AI aesthetic medicine identification and analysis module further feeds back and storing the real-time aesthetic medicine auxiliary evaluation result into the at least one of the medical knowledge rule module and the aesthetic medicine auxiliary evaluation result historical database.

3. The AI-assisted evaluation system according to claim 1, wherein the real-time aesthetic medicine auxiliary evaluation result at least contains an evaluated treatment site result combination and priority order for the subject, or the real-time aesthetic medicine auxiliary evaluation result at least contains the evaluated treatment site result combination and priority order and a type and a dose of an injected filler.

4. The AI-assisted evaluation system according to claim 1, wherein the medical knowledge rule module further comprises a functional medical anatomy rule and a dynamic medical anatomy rule.

5. The AI-assisted evaluation system according to claim 1, wherein the AI image detection process is performed according to an AI machine learning method, wherein the AI machine learning method includes a boundary detection algorithm corresponding to Haar-Like features in combination with an adaptive boosting machine learning method, or the AI machine learning method includes a histogram of oriented gradients (HOG) method in cooperation with a support vector machine (SVM) machine learning method.

6. The AI-assisted evaluation system according to claim 1, wherein before the AI facial action coding process is performed, a machine learning method is performed to train a facial action coding model of the AI facial action coding process according to a specified number of training data sets and a facial action coding system (FACS).

7. The AI-assisted evaluation system according to claim 6, wherein the facial action coding model is trained in different scenarios including a static expression scenario and/or a dynamic expression scenario, so that a static facial action coding information and a dynamic facial action coding information are respectively acquired.

8. The AI-assisted evaluation system according to claim 6, wherein before the AI facial emotion recognition process is performed, another machine learning method is employed to train a facial emotion recognition model of the AI facial emotion recognition process according to at least one of an emotional valance, an emotional arousal and the plural emotional indicators in combination with the above facial action coding system.

9. The AI-assisted evaluation system according to claim 1, wherein the AI image calibration and feature extraction unit comprises:

a facial key point labelling unit connected with the AI image detection unit, wherein the facial key point labelling unit performs an AI facial key point labelling process to acquire a facial key point labelling information;

a facial calibration and masking unit connected with the facial key point labelling unit, wherein the facial calibration and masking unit performs a facial image calibration process according to the facial key point labelling information, so that a normalized facial image information is acquired; and a facial feature extraction unit connected with the facial calibration and masking unit, wherein the facial feature extraction unit performs a facial image feature extraction process according to the facial key point labelling information and the normalized facial image information, so that the facial surface and geometric feature information is acquired.

10. The AI-assisted evaluation system according to claim 9, wherein before the AI facial key point labelling process is performed, a machine learning method is performed to train a facial key point model of the AI facial key point labelling process according to a specified number of training data sets.

11. The AI-assisted evaluation system according to claim 9, wherein the facial image feature extraction process at least comprises a facial image surface feature extraction process and a facial image geometric feature extraction process, wherein the facial image surface feature extraction process is performed through the histogram of oriented gradients (HOG) method to obtain multi-dimensional vector data, and a principal component analysis (PCA) technology is used to reduce a vector data amount and retain an important facial image surface feature information, wherein the facial image feature geometric extraction process is performed to acquire a facial image geometric feature information according to the facial key point labelling information.

12. The AI-assisted evaluation system according to claim 9, wherein the aesthetic medicine auxiliary evaluation result historical database contains plural aesthetic medical auxiliary evaluation results, wherein each of the plural aesthetic medical auxiliary evaluation results at least contains a subject name, a basic data, a historical face image emotion evaluation result, a personal facial feature, a functional medical anatomy rule and a dynamic medical anatomy rule of the medical knowledge rule module, an evaluated treatment site result combination and priority order and a type and a dose of an injected filler.

13. The AI-assisted evaluation system according to claim 12, wherein the personal facial feature contains a static texture feature, a static outline feature or a skin quality feature of an accustomed expression.

14. The AI-assisted evaluation system according to claim 12, wherein before the AI aesthetic medicine identification and analysis process is performed, at least one of an artificial neural network algorithm and a deep learning algorithm is performed to train an artificial intelligence model of the AI aesthetic medicine identification and analysis process according to the plural aesthetic medical auxiliary evaluation results.

15. The AI-assisted evaluation system according to claim 1, wherein the AI facial expression evaluation module, the AI aesthetic medicine identification and analysis module and the input/output module are assembled as an electronic device, wherein the electronic device is a handheld smart mobile device, a personal computer or a stand-alone smart device.

16. The AI-assisted evaluation system according to claim 15, wherein the electronic device is connected with at least one of the aesthetic medicine auxiliary evaluation result historical database and the medical knowledge rule module in at least one of a wireless transmission manner and a wired transmission manner.

\* \* \* \* \*